United States Patent [19]

Lemmen

[11] Patent Number: 5,417,645
[45] Date of Patent: May 23, 1995

[54] FLEXIBLE WRIST SPLINT FOR CARPAL TUNNEL SYNDROME TREATMENT

[76] Inventor: Roger D. Lemmen, 1241 Heather Dr., Holland, Mich. 49423

[21] Appl. No.: 158,420

[22] Filed: Nov. 29, 1993

[51] Int. Cl.⁶ .............................................. A61F 5/37
[52] U.S. Cl. ................................. 602/21; 602/20; 128/879; 128/878
[58] Field of Search .............. 602/21, 20, 62, 13, 602/6, 5, 64, 22; 128/878, 877, 879; 2/170, 910, 917

[56] References Cited

U.S. PATENT DOCUMENTS

| | | | |
|---|---|---|---|
| 2,206,404 | 7/1940 | Jones . | |
| 2,312,523 | 3/1943 | Corbett | 602/21 |
| 3,776,225 | 12/1973 | Lonardo | 602/21 |
| 4,138,108 | 2/1979 | Robinson . | |
| 4,549,537 | 10/1985 | Ender | 602/21 |
| 4,716,892 | 1/1988 | Brunswick . | |
| 4,782,825 | 11/1988 | Lonardo | 602/21 |
| 4,850,341 | 7/1989 | Fabry et al. . | |
| 4,854,309 | 8/1989 | Elsey . | |
| 4,862,877 | 9/1989 | Barber | 602/21 |
| 4,883,073 | 11/1989 | Aziz . | |
| 4,899,763 | 2/1990 | Sebastian et al. . | |
| 4,928,677 | 5/1990 | Barber | 602/21 |
| 4,941,460 | 7/1990 | Working . | |
| 4,960,114 | 10/1990 | Dale | 602/21 |
| 4,977,890 | 12/1990 | Mann | 602/21 |
| 5,014,689 | 5/1991 | Meunchen et al. . | |
| 5,056,504 | 10/1991 | Mann | 602/21 |
| 5,160,314 | 11/1992 | Peters . | |

*Primary Examiner*—Robert A. Hafer
*Assistant Examiner*—Michael O'Neill
*Attorney, Agent, or Firm*—Price, Heneveld, Cooper, DeWitt & Litton

[57] ABSTRACT

A flexible splint for use in the treatment of carpal tunnel syndrome includes an elongated, flexible member having a palmar portion and an elongated proximal portion. The palmar portion has a curved sickle or hook shape and defines a thumb notch. The palmar portion is angled with respect to the proximal portion to position the hand in a cocked up or near normal anatomical position. The flexible member is configured to avoid contact with the volar surface of the wrist which overlies the carpal tunnel. Elastic straps, including hook and loop fasteners, attach the splint to the wrist and palm of the user.

14 Claims, 2 Drawing Sheets

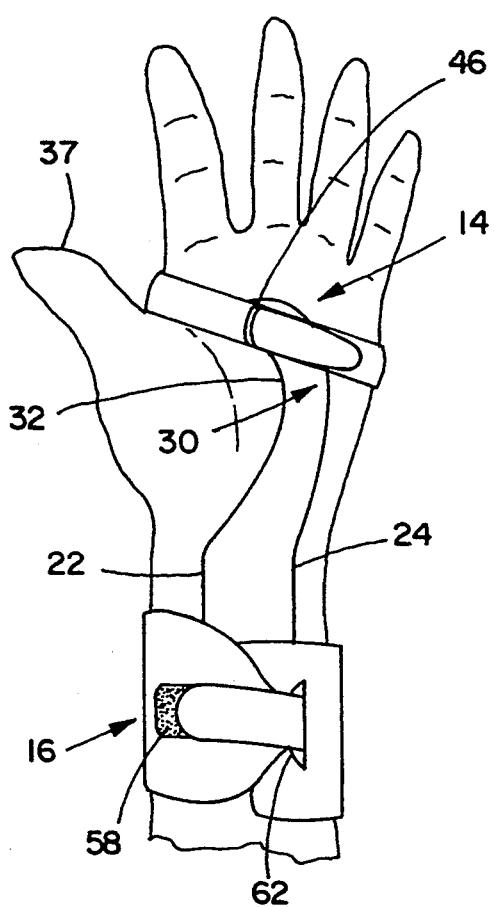
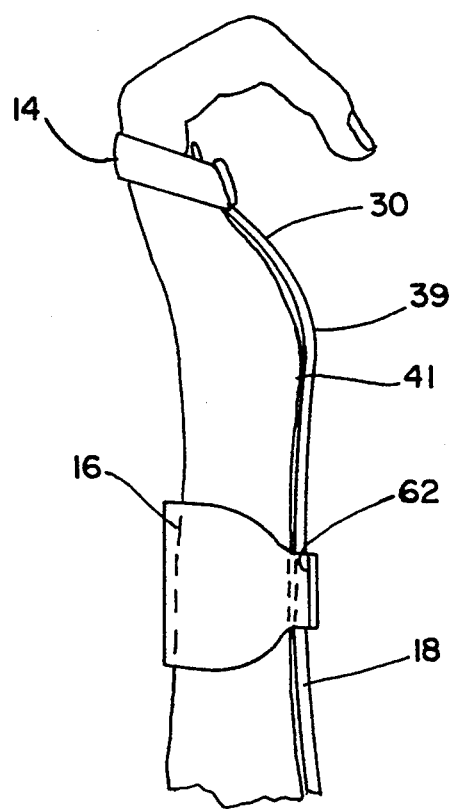
FIG. 4
FIG. 5

FLEXIBLE WRIST SPLINT FOR CARPAL TUNNEL SYNDROME TREATMENT

BACKGROUND OF THE INVENTION

The present invention relates to support devices or splints for the treatment of carpal tunnel syndrome.

Carpal tunnel syndrome is a painful condition associated with repetitive use of the hands and wrists. The condition is caused by compression of the median nerve as it passes through the carpal tunnel. Carpal tunnel syndrome is characterized by pain and paresthesia in the sensory distribution of the median nerve in the hand. Symptoms include numbness and tingling. A painful burning sensation in the fingers can radiate up the forearm to the shoulder.

Medical treatment is most effective when carpal tunnel syndrome is diagnosed early. U.S. Pat. No. 4,774,966 entitled CARPAL TUNNEL SYNDROME SCREENING DEVICE, which issued on Oct. 4, 1988 to the present inventor, discloses a device which permits such early diagnosis. Treatment has included splinting, medication or both. In severe cases, surgery may be necessary to relieve the pressure on the median nerve.

Typical splint or support arrangements restrict or prevent normal movement and use of the fingers and thumb. Prior devices may completely immobilize or prevent vertical movement of the hand with respect to the wrist. Immobilization may cause problems at the elbow and shoulder as the user compensates for the restricted movement. The discomfort associated with such prior splints and the adverse effects of long-term immobilization may limit use and proper treatment. Examples of prior splints, supports and the like for the wrist and hand may be found in U.S. Pat. No. 4,883,073 entitled REMEDIAL DEVICE FOR TREATMENT OF CARPAL TUNNEL SYNDROME, which issued on Nov. 28, 1989 to Aziz; U.S. Pat. No. 4,941,460 entitled CARPAL BRACE, which issued on Jul. 17, 1990 to Working; and U.S. Pat. No. 5,160,314 entitled WRIST SUPPORT, which issued on Nov. 3, 1992 to Peters.

A need exists for a splint useable in treating carpal tunnel syndrome which allows a full range of movement of the fingers and thumb, permits near normal hand function, is comfortable to use, acts more as a reminder of the correct, normal anatomical position, hence, providing movement to avoid stiffness caused by immobilization and which is easily applied by the user.

SUMMARY OF THE INVENTION

In accordance with the present invention, the aforementioned needs are fulfilled. Essentially, a splint is provided which includes an elongated, flexible member having a configured palmar portion and a proximal portion. The proximal portion lies in a single plane and the palmar portion is cocked up or angled with respect to the proximal portion to assist the user in maintaining the hand and wrist in a normal anatomical position. The palmar portion has a curved, hook or sickle shape and defines a thumb notch. The palmar portion is configured to extend along the palm of the user and terminates with an end pointing to the "V" between the thumb and index finger of the user. The flexible member is dimensioned so as to be positioned in spaced relationship with the joint between the thumb metacarpal and the trapezium of the distal carpal row and spaced from the metacarpal heads or palm crease to allow normal finger and thumb movement. The member is also configured to avoid or limit friction or contact with the volar surface of the wrist which overlies the carpal tunnel. Provision is made for attaching the flexible member to the user at the palm and wrist areas.

The splint allows normal motion of the hand but provides increased resistance to bending of the wrist the further the wrist is bent from the normal cocked up position. The splint acts as a reminder of the correct anatomical position while allowing near normal hand and wrist function and the maintenance of a more ergonomically preferred position. Flexibility is provided to allow movement and to avoid stiffness which would result from immobilization of the wrist and hand. The substantially unobstructed movement of the fingers and thumb lessens problems that can occur at the elbows and shoulders if such movement is limited. Increased movement at other joints to compensate for restrictions at the hand and wrist is not necessary.

BRIEF DESCRIPTION OF THE DRAWINGS

FIGS. 2 and 4 are a fragmentary, plan view showing the splint in position at the wrist and palm of the user; and FIGS. 3 and 5 are a side, elevational view showing a portion of the splint in position on the user.

DETAILED DESCRIPTION OF THE PREFERRED EMBODIMENT

Figure 1:
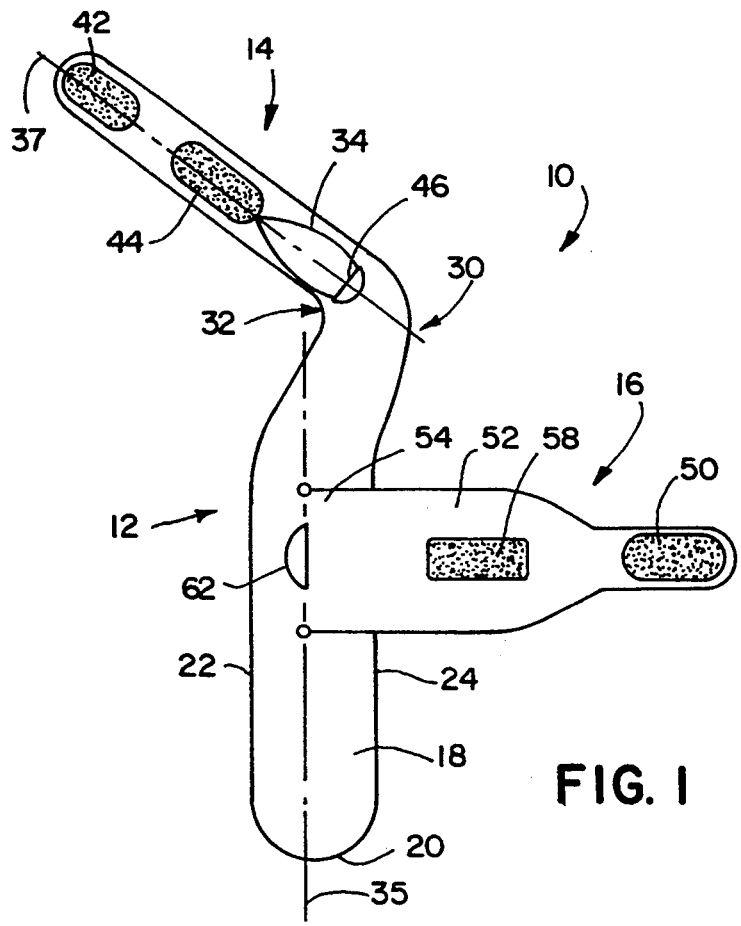
FIG. 1 is a plan view of a flexible splint in accordance with the present invention.

The preferred embodiment of a splint for use in the treatment of carpal tunnel syndrome in accordance with the present invention is illustrated in FIG. 1 and generally designated by the numeral 10. Splint 10 includes an elongated, resiliently flexible member 12, a palm attachment strap or palm strap 14 and a wrist attachment strap or wrist strap 16.

Member 12 has an elongated proximal portion 18 with a rounded proximal end 20 and spaced, generally parallel edges 22, 24. Portion 18 joins to a distal or palmar portion 30. Palmar portion 30 has a hook or sickle shape in plan and defines a thumb notch 32. Palmar portion 30 terminates in a distal end portion 34. End portion 34 is angled with respect to the longitudinal centerline 35 of proximal portion 18 of flexible member 12.

Figure 2:
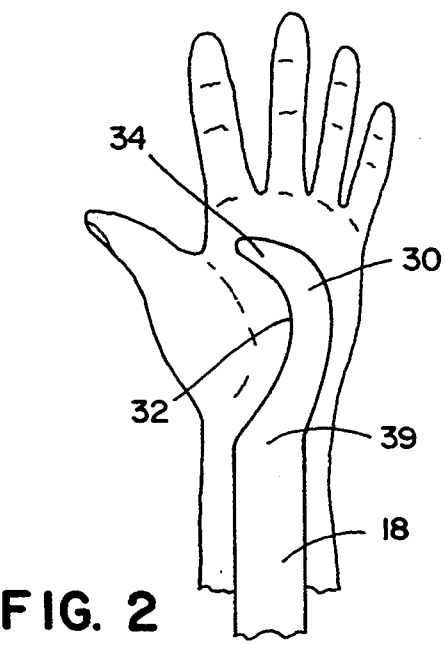
Figure 3:
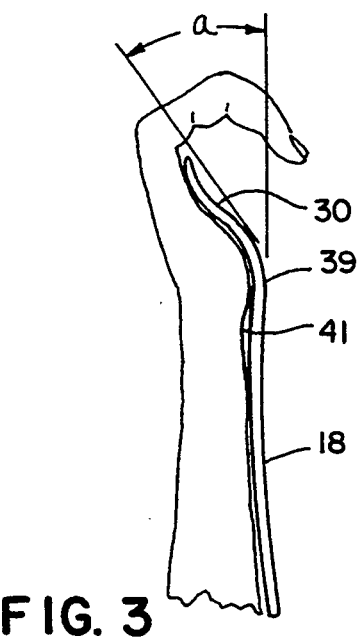

As seen in FIGS. 2 and 3, member 12 is placed against the palm of the hand and the underside of the wrist of the user. Proximal portion 18 extends over the wrist. Cutout 32 extends over the wrist in an attempt to minimize contact with the volar surface of the wrist which overlies the carpal tunnel. Also, as seen in FIG. 3, portions 18 and 30 at their juncture 39 are curved outwardly away from the wrist. The butt of the palm contacts the splint member, and portion 18 contacts the forearm spaced from the wrist. The splint defines a space 41 between the splint member and the volar surface of the wrist. The configuration avoids or minimizes contact between the splint and the wrist surface which overlies the carpal tunnel.

Palmar portion 30 is configured and dimensioned so that thumb notch 32 is spaced from the joint between the thumb metacarpal and the trapezium of the distal carpal row. In addition, the palmar portion is dimensioned to be spaced from the metacarpal heads and palmar crease of the hand so as not to interfere with movement of the fingers. Distal end portion 34 is angled so as to extend towards the "V" between the thumb and index finger when the hand is maintained in a normal, cocked up, anatomical position. As seen in FIG. 3, portion 30 extends at an angle "a" with respect to the horizontal plane of proximal portion 18. The angle is selected so that the splint and portion 30 functions as a reminder of the correct or normal anatomical position.

The flexible member permits movement of the hand and wrist or flexion of the wrist. Deviations from the normal anatomical position in either an up or down direction are, however, met with an increased resistance or force. The splint is resiliently flexible so as to bias the hand of the user toward the normal cocked up position. The splint will function, therefore, as a reminder of the proper positioning to relieve pressure on the median nerve associated with carpal tunnel syndrome.

Splint member 12 is attached to the wrist and hand of the user with palm strap 14 and wrist strap 16. Palm strap 14 is an elongated, elastic member which is physically attached to distal or end portion 34 of palmar portion 30 of member 12. The longitudinal axis 37 of the strap is coincident with the longitudinal axis of portion 34. Cooperating hook and loop fastener attachment strips 42, 44 are fixed to the same surface of strap 14. The strap will extend through the notch between the thumb and index finger of the user around the dorsal surface of the hand and back to the palmar surface. A loop 46 is included on member 12. The strap is passed through loop 46 and folded over and onto itself with fastener strips 42, 44 in engagement.

Wrist strap 16 is similar in construction. Strap 16 includes an elongated elastic member 52 which is joined to proximal portion 18 at an end 54. Cooperating hook and loop fastener strips 56, 58 are fixed to member 52. A loop 62 is fixed to portion 18. Attachment strap 16 is readily wrapped around the wrist or lower forearm of the user with its end passed through loop 62 and folded over with fastener strip 56 engaging fastener strip 58.

The splint may be relatively easily attached by the user. The splint is comfortable in use, which promotes wear during work, sleep or normal recreational activity. The splint allows near normal hand function in a more ergonomically preferred position. The splint acts as a reminder to the user to position the hand in the normal or neutral anatomical position. The elastic straps of attachment elements 14, 16 are readily washable. The unique configuration of the splint allows normal finger and thumb usage and movement and nearly unobstructed use of the hand and wrist. The splint lessens problems at other areas which would result from immobilizing the wrist and hand joints.

Elongated member 12 may be fabricated from any resilient material, such as an engineering plastic which returns to its initial position in a spring-like manner. The edges of the member should be rounded to promote comfort. The resilient bias or memory position of the member 12 provides an increased resistance to movement of the hand at the wrist in either the up or down direction.

In view of the above description, those of ordinary skill in the art may envision various modifications which would not depart from the inventive concepts disclosed herein. It is expressly intended, therefore, that the above description should be considered as only that of the preferred embodiment. The true spirit and scope of the present invention may be determined by reference to the appended claims.

The invention claimed is:

1. A splint for use in the treatment of carpal tunnel syndrome, comprising:

an elongated, flexible and resilient member having a palmar portion and a proximal portion, said palmar portion in plan view having a curved, hook-like shape dimensioned and configured to define a thumb notch, said palmar portion dimensioned and configured to extend only along the palm of the user in spaced relationship with the joint between the thumb metacarpal and the trapezium and spaced from the metacarpal heads to allow substantially normal and unobstructed finger and thumb movement, said member being fabricated of a material and shaped to resiliently bias the hand to a cocked up position and wherein said palmar portion is curved in side elevation and extends upwardly at an angle from said proximal portion, said member allowing flexion of the wrist yet resiliently biasing the hand to the normal anatomical position; and attachment means joined to said member for attaching the member to the palm and wrist of the user.

2. A splint as defined by claim 1 wherein said resilient member is configured at the juncture between the palmar portion and the proximal portion to define a space between the member and the volar surface of the wrist overlying the carpal tunnel.

3. A splint as defined by claim 2 wherein the hook-like shape of the palmar portion extends into the proximal portion of the member.

4. A splint as defined by claim 3 wherein said attachment means comprises:

an elongated palm strap extending from a distal end of said palmar portion; and fastener means on said palm strap for securing said palm strap after it is wrapped around the palm of the user.

5. A splint as defined by claim 4 wherein said attachment means further includes:

an elongated wrist strap extending from the proximal portion of said member; and fastener means on said wrist strap for securing said wrist strap after it is wrapped around the wrist of the user.

6. A splint as defined by claim 5 wherein said attachment means further includes a palm loop and a wrist loop on said elongated member.

7. A support device for use in the treatment and prevention of carpal tunnel syndrome, said device comprising:

an elongated, resilient splint member having a distal portion and a proximal portion, said portions dimensioned and configured so that said splint member extends along the underside of the forearm of the user, over the wrist and onto the palm, said distal portion having a generally curved shape in plan to define a thumb notch and an end portion angled towards the notch between the thumb and index finger of the user, said end portion configured so as to overlie the palm only of the user permitting substantially unobstructed finger and thumb movement, said splint member being fabricated form a resilient, spring-like material and being further configured in side elevation to bias the hand resiliently to a neutral anatomical position;

a palm strap attached to the end portion of the distal portion of said splint member; and a wrist strap attached to the proximal portion of said splint member, and wherein said splint member is curved and configured at a juncture between the distal and proximal portions to be out of contact with and to define a space between the splint member and the volar surface of the wrist which overlies the carpal tunnel of the user.

8. A support device as defined by claim 7 wherein said palm strap extends along the longitudinal axis of said end portion at an angle to the longitudinal axis of said proximal portion so as to attach the device to the palm by passing between the thumb and index finger and wrapping over the distal surface of the hand to the palmar surface.

9. A support device as defined by claim 8 further including fastener means on said palm strap for securing an end of said palm strap to said palm strap.

10. A support device for use in the treatment and prevention of carpal tunnel syndrome, said device comprising:

an elongated, resilient splint member having a distal portion and a proximal portion, said portions dimensioned so that said splint member extends along the underside of the forearm of the user, over the wrist and onto the palm, said distal portion having a generally curved shape in plan to define a thumb notch and an end portion angled towards the notch between the thumb and index finger of the user, said splint member being further configured in side elevation and being fabricated from a spring-like material to bias the hand resiliently to a neutral anatomical position;

a palm strap attached to the end portion of the distal portion of said splint member; and a wrist strap attached to the proximal portion of said splint member, and wherein said distal portion extends at an angle upwardly in side elevation from the plane of said proximal portion and wherein the juncture area between the proximal and distal portions is configured and curved in side elevation to define a space between the splint member and the volar surface of the wrist which overlies the carpal tunnel.

11. A support device as defined by claim 10 wherein said wrist strap extends perpendicular to the longitudinal axis of said proximal portion.

12. A support device as defined by claim 11 further including fastener means on said wrist strap for securing an end of said wrist strap to said wrist strap after wrapping around the wrist of the user.

13. A support device as defined by claim 12 wherein said palm strap has a longitudinal axis coincident with the longitudinal axis of said end portion and at an angle to the longitudinal axis of said proximal portion so as to attach the device to the palm by passing between the thumb and index finger and wrapping over the distal surface of the hand to the palmar surface.

14. A support device as defined by claim 13 further including fastener means on said palm strap for securing an end of said palm strap to said palm strap.

* * * * *